United States Patent [19]

Falling

[11] Patent Number: 5,406,007
[45] Date of Patent: Apr. 11, 1995

[54] PROCESS FOR THE PRODUCTION OF UNSATURATED ALCOHOLS

[75] Inventor: Stephen N. Falling, Kingsport, Tenn.

[73] Assignee: Eastman Chemical Company, Kingsport, Tenn.

[21] Appl. No.: 272,981

[22] Filed: Jul. 15, 1994

[51] Int. Cl.$^6$ ............... C07C 29/132; C07C 33/025; C07C 33/03; C07C 35/20

[52] U.S. Cl. .................... 568/908; 549/540; 568/483; 568/821; 568/849; 568/907

[58] Field of Search .............. 568/908, 821, 849

[56] References Cited

U.S. PATENT DOCUMENTS 2,561,984  7/1951  Hillyer et al. .
3,896,180  7/1975  Lemberg ........................ 568/821
4,962,210  10/1990  Falling et al. .

OTHER PUBLICATIONS

Zh. Obshch. Khim., 28, pp. 3046 and 3051 (1958).
"Study of the Hydrogenation of Unsaturated Epoxy Compounds", Neftekhimiya, V. 33, No. 2, pp. 131–137, 1993.

*Primary Examiner*—Joseph E. Evans
*Attorney, Agent, or Firm*—J. Frederick Thomsen; Harry J. Gwinnell

[57] ABSTRACT

Disclosed is a process for the conversion of conjugated epoxyalkenes to unsaturated alcohols wherein a conjugated epoxyalkene is catalytically hydrogenated in the presence of a sulfur-modified or sulfided nickel catalyst whereby the epoxide ring is hydrogenolyzed without concomitant hydrogenation of the olefinic unsaturation thereby producing allylic and/or homoallylic alcohols.

7 Claims, No Drawings

PROCESS FOR THE PRODUCTION OF UNSATURATED ALCOHOLS

This invention pertains to a novel process for the conversion of conjugated epoxyalkenes to unsaturated alcohols. More specifically, this invention pertains to the catalytic hydrogenation of conjugated epoxyalkenes by means of a sulfur-modified or sulfided nickel catalyst whereby the epoxide ring is hydrogenolyzed without concomitant hydrogenation of the olefinic unsaturation thereby producing allylic and/or homoallylic alcohols. By the term "conjugated epoxyalkene" is meant that the carbon-carbon double bond and the epoxide functional groups are adjacent, or stated another way, the epoxide oxygen is attached to the allylic carbon atom.

U.S. Pat. No. 4,897,498 describes an efficient process for the preparation of conjugated epoxyalkenes by the selective monoepoxidation of dienes, e.g., 3,4-epoxy-1-butene from 1,3-butadiene. A valuable compound which may be obtained from 3,4-epoxy-1-butene by the process of this invention is 2-buten-1-ol, more commonly referred to as crotyl alcohol.

Crotyl alcohol is a valuable chemical intermediate which finds utility in the production of crotyl halides, esters, and ethers, which in turn are valuable chemical intermediates in the production of monomers, fine chemicals, agricultural chemicals, and pharmaceuticals. The value of crotyl alcohol is suggested by the numerous references to the selective hydrogenation of crotonaldehyde to crotyl alcohol, e.g., J. Catalysis, 115, 65 (1989); J. Molecular Catalysis, 75, 71 (1992); Chemical Letters, 1345 (1992); and German. Offen. DE 2515422). Crotyl alcohol also is produced by the isomerization of 1,2-epoxybutane, for example, as described in Japanese Patent 47-013009 and U.S. Pat. Nos. 3,090,815, 3,090,816, and 3,542,883. The co-product from hydrogenation of 3,4-epoxy-1-butene by the process of this invention is 3-buten-1-ol, a chemical which finds utility as a fine chemical intermediate, e.g., in the production of 3,4-epoxy-1-butanol and 1,2,4-butanetriol. See, for example, German Offen. DE 87-3721495).

U.S. Pat. No. 5,077,418 discloses the selective double bond hydrogenation of conjugated epoxyalkenes to epoxyalkanes using rhodium catalysts, e.g., the hydrogenation of 3,4-epoxy-1-butene to 1,2-epoxybutane. The catalytic hydrogenation of 3,4-epoxy-1-butene to butyraldehyde over palladium and to 1-butanol over Raney-nickel is described in U.S. Pat. No. 2,561,984. The hydrogenation of 3,4-epoxy-1-butene also has been reported in Zh. Obshch. Khim., 28, 3046 and 3051 (1958) to give 1-butanol with platinum, palladium, and Raney-nickel catalysts. The authors state that crotyl alcohol was the. principle transient intermediate in the reduction, although butyraldehyde was also observed. A study of the hydrogenation of unsaturated epoxy compounds was reported in Neftekhimiya, 3, 131 (1993). wherein the authors observed initial conversion of 3,4-epoxy-1-butene to the unsaturated alcohols but that continued hydrogenation resulted in 1-butanol.

I have discovered that conjugated epoxyalkenes may be selectively hydrogenated in the presence of a sulfur-modified (sulfided) nickel catalyst whereby the epoxide ring is hydrogenolyzed without concomitant hydrogenation of the conjugated olefinic unsaturation. The present invention therefore provides a process for the preparation of an allylic alcohol, a homoallylic alcohol or a mixture thereof comprising hydrogenating an epoxyalkene wherein the epoxy and ethylenic unsaturation are conjugated in the presence of a sulfur-modified or sulfided nickel catalyst under hydrogenation conditions of temperature and pressure. The process of this invention is particularly useful for preparing crotyl alcohol (2-buten-1-ol) and 3-buten-1-ol by hydrogenating 3,4-epoxy-1-butene in the presence of a sulfur-modified or sulfided nickel catalyst. An important aspect of the process of this invention is that, under the preferred conditions of pressure and temperature, reduction virtually stops after formation of the unsaturated alcohols.

The significance of the conjugated epoxyalkene system in the reactants of this invention is demonstrated by the hydrogenation of 3,4-epoxy-1-butene and 1,2-epoxy-7-octene under mild conditions of 50°–55° C. and 4.6 bars hydrogen pressure using a sulfur-modified Raney-nickel catalyst. Such hydrogenation of 3,4-epoxy-1-butene gives 74% crotyl alcohol and 23% 3-buten-1-ol whereas the hydrogenation of 1,2-epoxy-7-octene (wherein the double bond and epoxy groups are separated by four carbon atoms) gives a mixture of starting material, 1,2-epoxyoctane, and isomers of the starting material.

The conjugated epoxyalkene reactants may contain from 4 to about 20 carbon atoms, preferably from 4 to 8 carbon atoms. Examples of the conjugated epoxyalkene reactants include compounds having the structural formula:

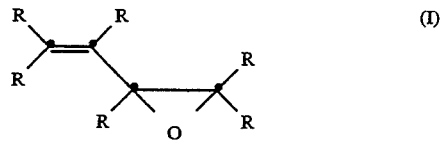

wherein each R is independently selected from hydrogen, alkyl of up to about 8 carbon atoms, a carbocyclic or heterocyclic aryl group of about 5 to 10 carbon atoms or halogen or any two R substituents collectively may represent an alkylene group forming a ring, e.g., alkylene containing in the main chain 4 to about 6 carbon atoms. The preferred epoxyalkene reactants comprise compounds of formula (I) wherein the R substituents individually represent hydrogen, lower alkyl, e.g., alkyl of up to about 4 carbon atoms, or collectively represent straight or branched chain alkylene of 4 to about 8 carbon atoms, especially compounds of formula (I) wherein at least 4 of the R groups represent hydrogen. Exemplary compounds contemplated for use in the practice of the present invention include 3,4-epoxy-1-butene, 3,4-epoxy-3-methyl-1-butene, 3,4-epoxy-2-methyl-1-butene, 2,3-dimethyl-3,4-epoxy-1-butene, 3,4-epoxycyclooctene, and the like. The epoxyalkene reactant of primary interest is 3,4-epoxy-1-butene.

The unsaturated alcohols produced in accordance with the present invention have the formulas:

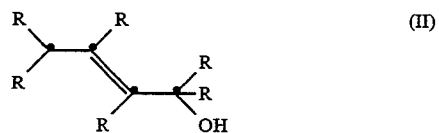

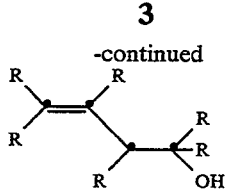

wherein the R substituents are defined above. Alcohols of formulas (II) and (III) are commonly known as allylic alcohols and homoallylic alcohols, respectively.

The sulfur-modified nickel catalyst which may be employed in the process include sulfur-modified Raney-nickel and sulfur-modified, supported nickel catalysts. The sulfur-modified, supported nickel catalyst may be comprised of about 10 to 80 weight percent, preferably, 25 to 65 weight percent, nickel, based on the total weight of the catalyst, deposited on the surface of a suitable catalyst support material. Typical catalyst supports include carbon, alumina, silica, silica-alumina, titania, kieselguhr, molecular sieves, zeolites, and the like. Nickel catalysts further modified or promoted with, for example, molybdenum, chromium, iron, zirconium, and/or cobalt also may be used.

The sulfur-modified or sulfided nickel catalysts may be prepared by treating Raney-nickel or a supported nickel catalyst, such as those described above, with a divalent sulfur compound according to known sulfiding procedures. Examples of sulfur compounds which may be used to provide the sulfur-modified catalysts employed in the present invention include hydrogen sulfide; carbon disulfide; $C_1$-$C_4$-alkyl thiols, e.g., methyl thiol; $C_1$-$C_4$-dialkyl sulfides, e.g., dimethyl sulfide; $C_1$-$C_4$-dialkyl disulfides, e.g., dimethyl disulfide; and aromatic sulfur compounds, e.g., thiophene. Modification of the nickel catalysts typically is carried out in the presence of a suitable liquid such as an alkanol. Modification of sulfiding of the untreated nickel catalyst may be performed as a separate process step in which the nickel is treated with a divalent sulfur compound and then isolated. Alternatively, treatment of the nickel catalyst may be performed as the initial step of the hydrogenation process wherein the sulfur modification of the catalyst is carried out in the hydrogenation vessel.

The hydrogenation conditions of temperature and pressure can vary substantially depending on several factors such as contact time with the sulfur-modified nickel catalyst, the particular catalyst and the amount thereof used, and the mode of operation. Hydrogenation temperatures of about 20° to 150° C. may be used although milder temperatures in the range of about 25° to 80° C. are advantageous to maximize conversion to the desired unsaturated alcohols and minimize over-reduction. The hydrogenation process may be carried out using total pressures in the range of about 2.4 to 415 bars absolute (20 to 6000 psig), preferably about 2.4 to 70 bars (20 to 1000 psig). The process pressures are set forth herein in bars absolute. As noted above, the optimum combination of temperature and pressure depends on other process variables but can be readily ascertained by those skilled in the art.

The process of this invention optionally may be carried out in the presence of an inert, organic solvent. Examples of such solvents include aliphatic and aromatic hydrocarbons such as cyclohexane, heptane, toluene, p-xylene and mixed xylene isomers, ethers such as tetrahydrofuran, $C_1$-$C_4$-alkanols such as methanol and ethanol, or the reaction products, e.g., crotyl alcohol and/or 3-buten-1-ol in the case of 3,4-epoxy-1-butene reactant. The process may be carried out in a batch, semi-continuous or continuous mode of operation. For example, batch operation may comprise agitating a slurry of a sulfur-modified nickel catalyst in 3,4-epoxy-1butene and, optionally, a solvent in a pressure vessel for a time sufficient to hydrogenate essentially all of the 3,4-epoxy-1-butene to crotyl alcohol and/or 3-buten-1-ol. The catalyst can be separated from the hydrogenated mixture by filtration and the components of the filtrate separated by distillation.

A preferred mode of operation uses a fixed bed of a supported, sulfur-modified nickel catalyst wherein the conjugated epoxyalkene is hydrogenated in the gas or, especially, liquid phase, optionally in the presence of an inert diluent or solvent. Liquid phase operation typically involves feeding a solution of the conjugated epoxyalkene in an inert solvent-diluent to the top of a columnar, pressure reactor containing one or more fixed beds of a supported, sulfur-modified nickel catalyst. The reactant solution flows (trickles) over the catalyst bed in the presence of hydrogen at elevated temperature and pressure and the hydrogenated product exits the bottom of the reactor and is separated into its components by distillation.

The process provided by the present invention is further illustrated by the following examples. Gas chromatographic (GC) analyses were performed on a Hewlett-Packard 5890A gas chromatograph with a 30 meter, DB-Wax, 0.32 mm inside-diameter, capillary column with a 0.5 micron film thickness. The temperature program was 35° C. (8 minutes), 5° C. per minute to 80° C., 20° C. per minute to 280° C., hold 17 minutes. The identities of the products obtained were confirmed by nuclear magnetic spectrometry and gas chromatography-mass spectrometry. The composition of the products obtained in the examples is given in weight percentages.

EXAMPLE 1

To a 500-mL pressure bottle was charged 15 g of water-wet Raney-nickel. The catalyst was rinsed 3 times with distilled water then 3 times with ethanol. To the catalyst was added 250 mL of ethanol and 60 drops of dimethyl disulfide. The mixture was allowed to stand for 5 minutes with occasional swirling. To the catalyst mixture was added 73.1 g (1.04 mole) of 3,4-epoxy-1-butene. The bottle was placed in a Parr, shaker-type hydrogenation apparatus and purged with nitrogen and then with hydrogen. The bottle was pressurized to 4.7 bars (54 psig) with hydrogen and agitation begun. The mixture was heated to 55° C. After 14 hours hydrogen uptake was complete. The catalyst was removed by filtration. GC analysis of the crude mixture showed (disregarding solvent): 74.2% crotyl alcohol (cis and trans isomers), 22.5% 3-buten-1-ol, 1.50% butyraldehyde, and 1.87% 1-butanol. The mixture was distilled to give: fraction 1, 25°–78° C., discarded; fraction 2, 78°–115° C., 3.8 g, GC: 17.1% crotyl alcohol, 11.7% 3-buten-1-ol, 0.04% butyraldehyde, 1.11% crotonaldehyde, 1.18% 1-butanol; fraction 3, 117°–121° C., 57.5 g, GC: 59.4% crotyl alcohol, 19.3% 3-buten-1-ol, 0.07% butyraldehyde, 1.26% crotonaldehyde, 2.57% 1-butanol. The weight of unsaturated alcohols on a 100% basis was 48.27 g (64.2% yield).

EXAMPLE 2

To a 250-mL pressure bottle was charged 3 g of water-wet Raney-nickel. The catalyst was rinsed 3 times with distilled water, 3 times with ethanol then 3 times with cyclohexane. To the catalyst was added 50 mL of cyclohexane and 6 drops of carbon disulfide. The mixture was allowed to stand for 5 minutes with occasional swirling. To the catalyst mixture was added 14.31 g (0.204 mole) of 3,4-epoxy-1-butene and 1.25 g of diglyme (internal standard). The bottle was placed in a Parr, shaker-type hydrogenation apparatus and purged with nitrogen and then with hydrogen. The bottle was pressurized to 4.7 bars (53 psig) with hydrogen and agitation begun. The mixture was heated to 70° C. for 9 hours. The catalyst was removed by filtration. GC analysis of the crude mixture showed (disregarding solvent): 54.5% crotyl alcohol (cis and trans isomers), 14.5% 3-buten-1-ol, 7.92% butyraldehyde, 0.03% 3,4-epoxy-1-butene, 0.07% crotonaldehyde, and 4.27% 1-butanol.

EXAMPLE 3

To a 250-mL pressure bottle was charged 3 g of water-wet molybdenum-promoted Raney-nickel (W. R. Grace Raney-nickel 3100). The catalyst was rinsed 3 times with distilled water then 3 times with ethanol. To the catalyst was added 50 mL of ethanol and 6 drops of carbon disulfide. The mixture was allowed to stand for 5 minutes with occasional swirling. To the catalyst mixture was added 14.59 g (0.208 mole) of 3,4-epoxy-1-butene and 1.18 g of diglyme (internal standard). The bottle was placed in a Parr, shaker-type hydrogenation apparatus and purged with nitrogen then with hydrogen. The bottle was pressurized to 4.8 bar (55 psig) with hydrogen and agitation begun. The mixture was heated to 70° C. for 13 hours. The catalyst was removed by filtration. GC analysis of the crude mixture showed (disregarding solvent): 52.7% crotyl alcohol (cis and trans isomers), 15.2% 3-buten-1-ol, 3.84% butyraldehyde, 0.10% 3,4-epoxy-1-butene, 0.80% crotonaldehyde, and 1.92% 1-butanol.

EXAMPLE 4

To a 250-mL pressure bottle was charged 3.3 g of water-wet Raney-nickel. The catalyst was rinsed 3 times with distilled water then 3 times with ethanol. To the catalyst was added a solution of ethanolic hydrogen sulfide (17 mL ethanol saturated with hydrogen sulfide (approximately 0.2 g) diluted to 50 mL with ethanol). The mixture was allowed to stand for 5 minutes with occasional swirling. To the catalyst mixture was added 14.52 g (0.207 mole) of 3,4-epoxy-1-butene and 1.18 g of diglyme (internal standard). The bottle was placed in a Parr, shaker-type hydrogenation apparatus and purged with nitrogen and then with hydrogen. The bottle was pressurized to 4.7 bars (54 psig) with hydrogen and agitation begun. The mixture was heated to 70° C. for 6.8 hours while samples were taken periodically and analyzed by GC. The amounts of 1,2-epoxybutane, 3,4-epoxy-1-butene, butyraldehyde, 1-butanol, 3-buten-1-ol, crotonaldehyde and crotyl alcohol present in the reaction mixture after 60, 155, 300, 410 and 1220 minutes at the above-described hydrogenation conditions are shown in Table I. GC analysis of the crude mixture after 410 minutes showed (disregarding solvent): 56.3% crotyl alcohol (cis and trans isomers), 15.2% 3-buten-1-ol, 1.39% butyraldehyde, 0.88% 3,4-epoxy-1-butene, 1.87% crotonaldehyde, and 0.84% 1-butanol. The reduction was continued for another 13.5 hours but with little additional hydrogen uptake. The catalyst was removed by filtration. GC analysis of the crude mixture showed (disregarding solvent): 54.0% crotyl alcohol (cis and trans isomers), 13.0% 3-buten-1-ol, 4.47% butyraldehyde, 0.04% 3,4-epoxy-1-butene, 0.22% crotonaldehyde, and 5.92% 1-butanol. This example and the data set forth in Table I show that no substantial reduction of the unsaturated alcohol products occurs after their formation.

TABLE I

| Time (Min.) | 1,2-Epoxy-Butane | 3,4-Epoxy-1-Butene | Butyraldehyde | 1-Butanol | 3-Buten-1-ol | Croton-Aldehyde | Crotyl Alcohol |
| --- | --- | --- | --- | --- | --- | --- | --- |
| 0 | 0.00 | 90.7 | 0.00 | 0.03 | 0.00 | 0.14 | 0.07 |
| 60 | 0.04 | 61.5 | 0.15 | 0.07 | 3.69 | 1.04 | 17.7 |
| 155 | 0.07 | 38.4 | 0.26 | 0.18 | 7.89 | 1.61 | 32.0 |
| 300 | 0.11 | 13.3 | 0.55 | 0.44 | 12.7 | 1.94 | 48.1 |
| 410 | 0.11 | 0.88 | 1.39 | 0.84 | 15.2 | 1.87 | 56.3 |
| 1220 | 0.00 | 0.04 | 4.47 | 5.92 | 13.0 | 0.22 | 54.0 |

EXAMPLE 5

Water-wet Raney-nickel (6 g) was rinsed 3 times with distilled water then 3 times with ethanol. To the catalyst was added 100 mL of ethanol and 24 drops of dimethyl disulfide. The mixture was allowed to stand for 5 minutes with occasional swirling. To the catalyst mixture was added 28.9 g (0.412 mole) of 3,4-epoxy-1-butene. The mixture was placed in an autoclave and purged with nitrogen then with hydrogen. The autocalve was pressurized to 70 bars (1000 psig) with hydrogen and agitation begun. The mixture was heated to 55° C. for 6 hours while samples were taken periodically and analyzed by GC. The amounts of 1,2-epoxybutane, 3,4-epoxy-1-butene, butyraldehyde, 1-butanol, 3-buten-1-ol, crotonaldehyde and crotyl alcohol present in the reaction mixture after 5, 30, 60, 90, 120, 180, 240, 300 and 360 minutes at the above-described hydrogenation conditions are shown in Table II. GC analysis of the reaction mixture at the end of the hydrogenation period showed (disregarding solvent): 63.7% crotyl alcohol (cis and trans isomers), 13.9% 3-buten-1-ol, 3.44% butyraldehyde, 0.04% 3,4-epoxy-1-butene, 0.19% crotonaldehyde, and 6.76% 1-butanol. This example and the data presented in Table II show that no substantial reduction of the unsaturated alcohol products occurs after their formation at high pressure.

TABLE II

| Time (Min.) | 1,2-Epoxy-Butane | 3,4-Epoxy-1-Butene | Butyraldehyde | 1-Butanol | 3-Buten-1-ol | Croton-Aldehyde | Crotyl Alcohol |
| --- | --- | --- | --- | --- | --- | --- | --- |
| 0 | 0.00 | 96.8 | 0.03 | 0.00 | 0.03 | 0.20 | 0.07 |
| 5 | 0.00 | 86.9 | 0.04 | 0.04 | 0.96 | 0.41 | 2.74 |

TABLE II-continued

| Time (Min.) | 1,2-Epoxy-Butane | 3,4-Epoxy-1-Butene | Butyraldehyde | 1-Butanol | 3-Buten-1-ol | Croton-Aldehyde | Crotyl Alcohol |
|---|---|---|---|---|---|---|---|
| 30 | 0.04 | 25.9 | 1.23 | 1.69 | 12.5 | 0.58 | 46.1 |
| 60 | 0.00 | 0.04 | 1.90 | 3.06 | 17.3 | 0.19 | 65.4 |
| 90 | 0.00 | 0.04 | 2.11 | 3.38 | 17.5 | 0.19 | 66.1 |
| 120 | 0.00 | 0.04 | 2.16 | 3.76 | 16.6 | 0.19 | 65.5 |
| 180 | 0.00 | 0.04 | 2.54 | 4.58 | 16.0 | 0.19 | 64.8 |
| 240 | 0.00 | 0.04 | 2.91 | 5.32 | 15.3 | 0.19 | 64.2 |
| 300 | 0.00 | 0.04 | 3.19 | 6.14 | 14.5 | 0.20 | 63.7 |
| 360 | 0.00 | 0.04 | 3.44 | 6.76 | 13.9 | 0.19 | 63.7 |

EXAMPLE 6

To a 250-mL pressure bottle was charged 3.0 g of water-wet Raney-nickel. The catalyst was rinsed 3 times with distilled water then 3 times with ethanol. To the catalyst was added 50 mL of ethanol and 12 drops of dimethyl disulfide. The mixture was allowed to stand for 5 minutes with occasional swirling. To the catalyst mixture was added 8.74 g (0.104 mole) of a 95.5/4.5 mixture of 3,4-epoxy-3-methyl-1-butene/3,4-epoxy-2-methyl-1-butene. The bottle was placed in a Parr, shaker-type hydrogenation apparatus and purged with nitrogen then with hydrogen. The bottle was pressurized to 4.5 bars (51 psig) with hydrogen and agitation begun. The mixture was heated to 50° C. After 2.5 hours hydrogen uptake was complete. The catalyst was removed by filtration. GC analysis of the crude mixture showed (disregarding solvent): 62.4% 2-methyl-2-buten-1-ol (cis and trans isomers), 12.5% 2-methyl-3-buten-1-ol, 1.19% 3-methyl-3-buten-1-ol, 3.28% 2-methylbutyraldehyde. The mixture was distilled to give: fraction 1 25°–90° C., discarded; fraction 2, 90°–118° C. discarded; fraction 3, 118°–124° C. 1.78 g, GC: 63.3% 2-methyl-2-buten-1-ol (cis and trans isomers), 27.9% 2-methyl-3-buten-1-ol, 1.89% 3-methyl-3-buten-1-ol, 3.26% 2-methylbutyraldehyde; fraction 4, 124°–131° C. 4 06 g, GC: 90.1% 2-methyl-2-buten-1-ol (cis and trans isomers), 6.89% 2-methyl-3-buten-1-ol, 1.27% 3-methyl-3-buten-1-ol, 0.40% 2-methylbutyraldehyde. The weight of unsaturated alcohols on a 100% basis was 5.56 g (62.1% yield).

EXAMPLE 7

To a 250-mL pressure bottle was charged 0.80 g of water-wet Raney-nickel. The catalyst was rinsed 3 times with distilled water then 3 times with ethanol. To the catalyst was added 15 mL of ethanol and 3 drops of dimethyl disulfide. The mixture was allowed to stand for 5 minutes with occasional swirling. To the catalyst mixture was added 1.38 g (0.0111 mole) of 3,4-epoxycyclooctene. The bottle was placed in a Parr, shaker-type hydrogenation apparatus and purged with nitrogen then with hydrogen. The bottle was pressurized to 4.5 bars (50 psig) with hydrogen and agitation begun. The mixture was heated to 55° C. for 8 hours. The catalyst was removed by filtration. The solvent was removed by rotary evaporation (up to about 40° C. and 30 torr) to give 1.39 g of product. GC, GC-MS and NMR analysis showed the product to be 49.3% cyclooct-2-en-1-ol and 38.4% cyclooct-3-en-1-ol. The weight of unsaturated alcohols on a 100% basis was 1.22 g (87.1% yield).

COMPARATIVE EXAMPLE 1

This example shows the effect of a non-sulfur-modified nickel catalyst on the hydrogenation of a conjugated epoxyalkene. To a 250-mL pressure bottle was charged 0.45 g of water-wet Raney-nickel. The catalyst was rinsed 3 times with distilled water then 3 times with ethanol. To the catalyst was added 50 mL of ethanol followed by 14.8 g (0.210 mole) of 3,4-epoxy-1-butene. The bottle was placed in a Parr, shaker-type hydrogenation apparatus and purged with nitrogen then with hydrogen. The bottle was pressurized to 4.5 bars (50 psig) with hydrogen and agitation begun. The mixture was heated to 55° C. for 17 hours while samples were taken periodically and analyzed by GC. The amounts of 1,2-epoxybutane, 3,4-epoxy-1-butene, butyraldehyde, 1-butanol, 3-buten-1-ol, crotonaldehyde and crotyl alcohol present in the reaction mixture after 47, 91, 141, and 1025 minutes at the above-described hydrogenation conditions are shown in Table III. The catalyst was removed by filtration. GC analysis of the final, crude reaction mixture showed (disregarding solvent): 0.15% crotyl alcohol, 0% 3-buten-1-ol, 18.1% 1,2-epoxybutane, 0.38% 2-butanol, and 77.6% 1-butanol.

TABLE III

| Time (Min.) | 1,2-Epoxy-Butane | 3,4-Epoxy-1-Butene | Butyraldehyde | 1-Butanol | 3-Buten-1-ol | Croton-Aldehyde | Crotyl Alcohol | 2-Butanol |
|---|---|---|---|---|---|---|---|---|
| 0 | 0.00 | 97.6 | 0.00 | 0.00 | 0.03 | 0.21 | 0.03 | 0.00 |
| 47 | 5.47 | 71.4 | 1.30 | 2.40 | 5.01 | 0.70 | 11.0 | 0.00 |
| 91 | 9.21 | 52.0 | 2.52 | 5.22 | 8.34 | 0.98 | 18.8 | 0.00 |
| 141 | 13.0 | 32.3 | 4.00 | 9.15 | 11.11 | 1.11 | 26.2 | 0.00 |
| 1025 | 18.1 | 0.00 | 0.00 | 77.6 | 0.00 | 0.11 | 0.15 | 0.38 |

COMPARATIVE EXAMPLE 2

This example shows the effect of a non-sulfur-modified nickel catalyst on the hydrogenation of a nonconjugated epoxyalkene. Water-wet Raney-nickel (1.03 g) was placed in a 250-mL pressure bottle and rinsed 3 times with tetrahydrofuran. To the catalyst was added 50 mL of tetrahydrofuran followed by 12.72 g (0.1008 mole) of 1,2-epoxy-7-octene. The bottle was placed in a Parr, shaker-type hydrogenation apparatus and purged with nitrogen then with hydrogen. The bottle was pressurized to 4.5 bars (50 psig) with hydrogen and agitation begun. The mixture was heated to 50° C. The fast hydrogenation took up one equivalent of hydrogen in 30 minutes but the reaction conditions were continued for a total of 4 hours. GC analysis of the crude mixture showed (disregarding solvent): 94.4% 1,2-epoxyoctane, 0.05% 1,2-epoxy-7-octene, 1.18% 1-octanol, and 0% 2-octanol.

COMPARATIVE EXAMPLE 3

This example shows the effect of a sulfur-modified nickel catalyst on the hydrogenation of a nonconjugated epoxyalkene. Water-wet Raney-nickel (3.5 g) was charged to a 250-mL pressure bottle and rinsed 3 times with distilled water, then 3 times with ethanol. To the catalyst was added 50 mL of ethanol followed by 12.8 g (0.102 mole) of 1,2-epoxy-7-octene. The bottle was placed in a Parr, shaker-type hydrogenation apparatus and purged with nitrogen then with hydrogen. The bottle was pressurized to 4.5 bars (50 psig) with hydrogen and agitation begun. The mixture was heated to 50° C. Little take-up of hydrogen was detected by pressure change over a period of 8 hours. GC analysis of the final crude reaction mixture showed (disregarding solvent): 77.3% 1,2-epoxy-7-octene, 9.49% and 6.71% double bond isomers of starting material, and 6.50% 1,2-epoxyoctane.

The invention has been described in detail with particular reference to preferred embodiments thereof, but it will be understood that variations and modifications can be effected within the spirit and scope of the invention.

I claim:

1. Process for the preparation of an allylic alcohol, a homoallylic alcohol or a mixture thereof comprising hydrogenating an epoxyalkene wherein the epoxy and ethylenic unsaturation are conjugated in the presence of a sulfur-modified or sulfided nickel catalyst under hydrogenation conditions of temperature and pressure.

2. Process according to claim 1 wherein the conjugated epoxyalkene reactants contain from 4 to about 8 carbon atoms and have the formula:

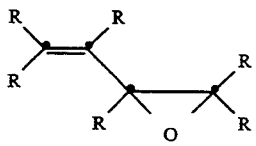

(I)

wherein each R is independently selected from hydrogen, lower alkyl, or collectively represent straight or branched chain alkylene of 4 to about 8 carbon atoms.

3. Process according to claim 2 wherein the hydrogenation conditions of temperature and pressure comprise a temperature of about 20° to 150° C. and a pressure of about 2.4 to 415 bars absolute.

4. Process for the preparation of a mixture of alcohols having the formulas

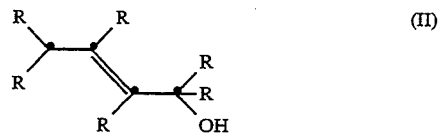

(II)

and

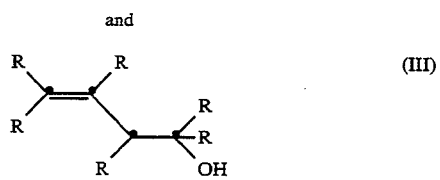

(III)

which comprises hydrogenating a conjugated epoxyalkene having the formula

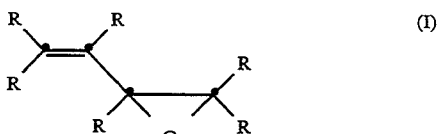

(I)

in the presence of a sulfur-modified nickel catalyst at a temperature of about 25° to 80° C. and a pressure of about 2.4 to 70 bars absolute;
wherein the R substituents individually represent hydrogen, lower alkyl, or collectively represent straight or branched chain alkylene of 4 to about 8 carbon atoms, and wherein at least 4 of the R groups represent hydrogen.

5. Process according to claim 4 wherein the catalyst is sulfur-modified Raney nickel.

6. Process according to claim 4 wherein the catalyst is a sulfur-modified supported nickel catalyst wherein nickel constitutes about 25 to 65 weight percent of the total weight of the catalyst.

7. Process for the preparation of a mixture of crotyl alcohol (2-buten-1-ol) and 3-buten-1-ol by hydrogenating 3,4-epoxy-1-butene in the presence of a sulfur-modified nickel catalyst selected from sulfur-modified Raney nickel and sulfur-modified supported nickel catalysts wherein nickel constitutes about 25 to 65 weight percent of the total weight of the catalyst at a temperature of about 25° to 80° C. and a pressure of about 2.4 to 70 bars absolute.

* * * * *